US007101363B2

(12) United States Patent
Nishizawa et al.

(10) Patent No.: US 7,101,363 B2
(45) Date of Patent: Sep. 5, 2006

(54) MEDICAL MANIPULATOR HAVING A PLURALITY OF JOINTS

(75) Inventors: Kouji Nishizawa, Kokubunji (JP); Fujio Tajima, Tsuchiura (JP); Kosuke Kishi, Chiyoda (JP)

(73) Assignee: Hitachi, Ltd., Tokyo (JP)

( * ) Notice: Subject to any disclaimer, the term of this patent is extended or adjusted under 35 U.S.C. 154(b) by 223 days.

(21) Appl. No.: 10/675,985

(22) Filed: Oct. 2, 2003

(65) Prior Publication Data

US 2004/0199147 A1 Oct. 7, 2004

(30) Foreign Application Priority Data

Oct. 2, 2002 (JP) ............................. 2002-289359

(51) Int. Cl.
*A61B 17/00* (2006.01)
*A61B 17/28* (2006.01)
*A61B 17/42* (2006.01)
*A61B 17/44* (2006.01)

(52) U.S. Cl. .................... 606/1; 606/205; 606/206; 606/207; 606/208

(58) Field of Classification Search .............. 606/1, 606/205–208, 130
See application file for complete search history.

(56) References Cited

U.S. PATENT DOCUMENTS 5,549,636 A * 8/1996 Li ............................ 606/206
5,710,870 A * 1/1998 Ohm et al. ................. 700/263
5,797,900 A    8/1998 Madhani et al.
5,810,880 A * 9/1998 Jensen et al. ............... 606/205
6,206,903 B1 * 3/2001 Ramans ..................... 606/205
6,394,998 B1 * 5/2002 Wallace et al. ............. 606/1
6,554,844 B1 * 4/2003 Lee et al. ................... 606/130

* cited by examiner

*Primary Examiner*—Michael Peffley
*Assistant Examiner*—Alex Toy
(74) *Attorney, Agent, or Firm*—Antonelli, Terry, Stout and Kraus, LLP.

(57) ABSTRACT

A manipulator for medical use having a reduced size and improved controllability. The manipulator includes a surgical tool portion, a grip portion provided on the surgical tool portion, and a driver portion for driving the grip portion provided on the surgical tool portion. A connection portion of the surgical tool is provided between the surgical tool portion and the driver portion. The surgical tool can be separated from, and connected to, the driver portion. The surgical tool portion has two rotating members disposed in opposing relation to each other. A driving arrangement is provided for driving one of the rotating members and causing it to revolute the other rotating member, but not rotate by itself. An arrangement is also provided for keeping a distance between rotation centers of the two rotating members constant.

7 Claims, 11 Drawing Sheets

MEDICAL MANIPULATOR HAVING A PLURALITY OF JOINTS

BACKGROUND OF THE INVENTION

The present invention relates to a manipulator, and in particular, to a manipulator being suitable for use in medical applications.

The manipulators relating to the conventional arts are shown, for example, in U.S. Pat. No. 5,797,900 (Patent Document 1) and U.S. Pat. No. 6,394,998 (Patent Document 2). The manipulator for medical application described in Patent Document 1, uses wires for moving a wrist joint. The position of an actuator, which drives a surgical instrument locating at the tip of the manipulator, is controlled depending on changes in route lengths of the wires. Namely, since the route lengths of the wire change on an inside and an outside of the joint when a first joint is moved on the actuator side, then with using the wires for moving a second joint on the anti-actuator side, also drives the first joint. Also with the Patent Document 2, a joint at a tip portion of a manipulator for medical application, and also a surgical tool provided at a further tip portion of this joint, as well, are rotationally driven or opened/closed by using wires.

For the instruments or tools located at the tip portion of the manipulators for the medical application, there is a requirement that they be small size in, and have plural number of degrees of freedom. In each of the Patent Documents mentioned above, driving force is transmitted through the wire from the actuator to the surgical instrument or tool. However, with such a configuration in which the opening/closing of the manipulator or the surgical tool is driven using the wires, the routes of the wires are changed when an angle of the joint is varied, and there is a risk that the joint cannot perform an oscillating or swinging operation. For dissolving such the drawback, with the Patent Document 1, the joint angle at the tip portion side is controlled by using the driving force due to the change in the route lengths of the wires. For this reason, there is a necessity of controlling a position of a motor, which builds up the actuator.

Also, with the surgical tools described in the Patent Document 2, cooperative control is necessary for the actuators themselves. However, if the cooperative control cannot be done well, tension is applied on the wires too much more than necessity, and there is a possibility that the lifetime of the wires are shortened.

BRIEF SUMMARY OF THE INVENTION

According to the present invention, being achieved by taking the drawbacks of the conventional arts into the consideration, an object thereof is to provide a manipulator for medical application or use, that is small in size and rich in controllability. Another object of the present invention is to provide a manipulator, to which the surgical tool or instrument can be attached/detached with ease.

For accomplishing the object mentioned above, according to the present invention, first there is provided a manipulator having a plural number of joints therein, wherein at least in one (1) joint of said joints, comprises: two (2) pieces of rotating members, being disposed opposing to each other; a driving means for driving one of said rotating members to make a rotating movement to the other thereof; and a means for keeping a distance between rotation centers of said two (2) pieces of rotating members to be constant.

According to the present invention, in the manipulator as described above, preferably: said driving means has a guide means (i.e., a middle plate) attached on a rotation shaft of each of said rotting members, and a wire fixed at least at one (1) point thereof onto said guide means; said joint is a second one from a tip thereof or thereafter, and a wire for driving the joint locating nearer to said tip portion is guided to the joint on a side of the tip portion, passing through between said guide members owned by said joint; and, said rotating members is made up with at least one of the followings; a gear, on a rotating portion of which are formed a plural number of teeth; a means having a semicircular portion, on which a hardening surface treatment is conducted; means being treated with surface processing having viscosity or adhesiveness on surfaces in contact with each other; a means having wire holding means disposed opposing to each other and two (2) pieces of wires, each being fixed on said different wire holding means at both end portions thereof, while crossing said two (2) pieces of wires with each other.

Further, according to the present invention, for accomplishing the object mentioned above, there is also provided a manipulator, comprising: a surgical tool portion; a grip portion provided on said surgical tool portion; and a driver portion for driving said griping portion provided on said surgical tool portion, wherein a surgical tool connection portion is provided between said surgical tool portion and said driver portion, and said surgical tool portion can be separated from or connected to, between said driver portion and said surgical tool connection portion.

According to the present invention, in the manipulator as described in the above, preferably, said surgical tool connection portion has a plural number of first guiding means for guiding wires for driving a grip portion, wires being guided by means of said first guiding means, and a second guiding means being formed with a pulley for holding a portion of said wires, wherein said driving portion has a third guiding means being in contact with said second guiding means, and a driving means for driving said third guiding means.

Also, according to the present invention, in the manipulator as described in the above: preferably, a tension detecting means is provided in a middle of said wire; further comprises therein means for controlling an amount of pulling said wire by means of said driving means; and, said surgical tool connection portion has a pin extending to an end portion side thereof, while forming a hole in said driver portion for inserting said pin therein, whereby positioning said driver portion and said surgical tool connection portion. Further, it is preferable, there is further provided a screw means for connecting said surgical tool connection portion and said driver portion, forming a hole in a central portion of said surgical tool connection portion, and also hole at a position corresponding to said hole in said driver portion, respectively.

Further, according to the present invention, for accomplishing the object mentioned above, there is provided a manipulator, comprising: a surgical tool portion; a grip portion provided on said surgical tool portion; and a driver portion for driving said griping portion provided on said surgical tool portion, wherein a surgical tool connection portion is provided between said surgical tool portion and said driver portion, and said surgical tool portion can be separated from or connected to, between said driver portion and said surgical tool connection portion, and said surgical tool connection portion has a joint for rotating said grip portion, wherein said joint has: two (2) pieces of rotating members, being disposed opposing to each other; a driving means for driving one of said rotating members to make a rotating movement to the other thereof; and a means for keeping a distance between rotation centers of said two (2) pieces of rotating members to be constant.

Also, further according to the present invention, there is provided a manipulator, comprising: a joint having a first link and a second link therein; a rotating contact means for bringing said first and second links to rotate while being in contact with each other; a guide means for guiding a wire at an equal distance from each rotation center of said links when they rotate while being in contact with each other; and said wire being guided by said guide means, wherein said wire is wired passing through between said guide means.

BRIEF DESCRIPTION OF THE SEVERAL VIEWS OF THE DRAWING

Those and other objects, features and advantages of the present invention will become more readily apparent from the following detailed description when taken in conjunction with the accompanying drawings wherein.

DETAILED DESCRIPTION OF THE INVENTION

Figure 1:
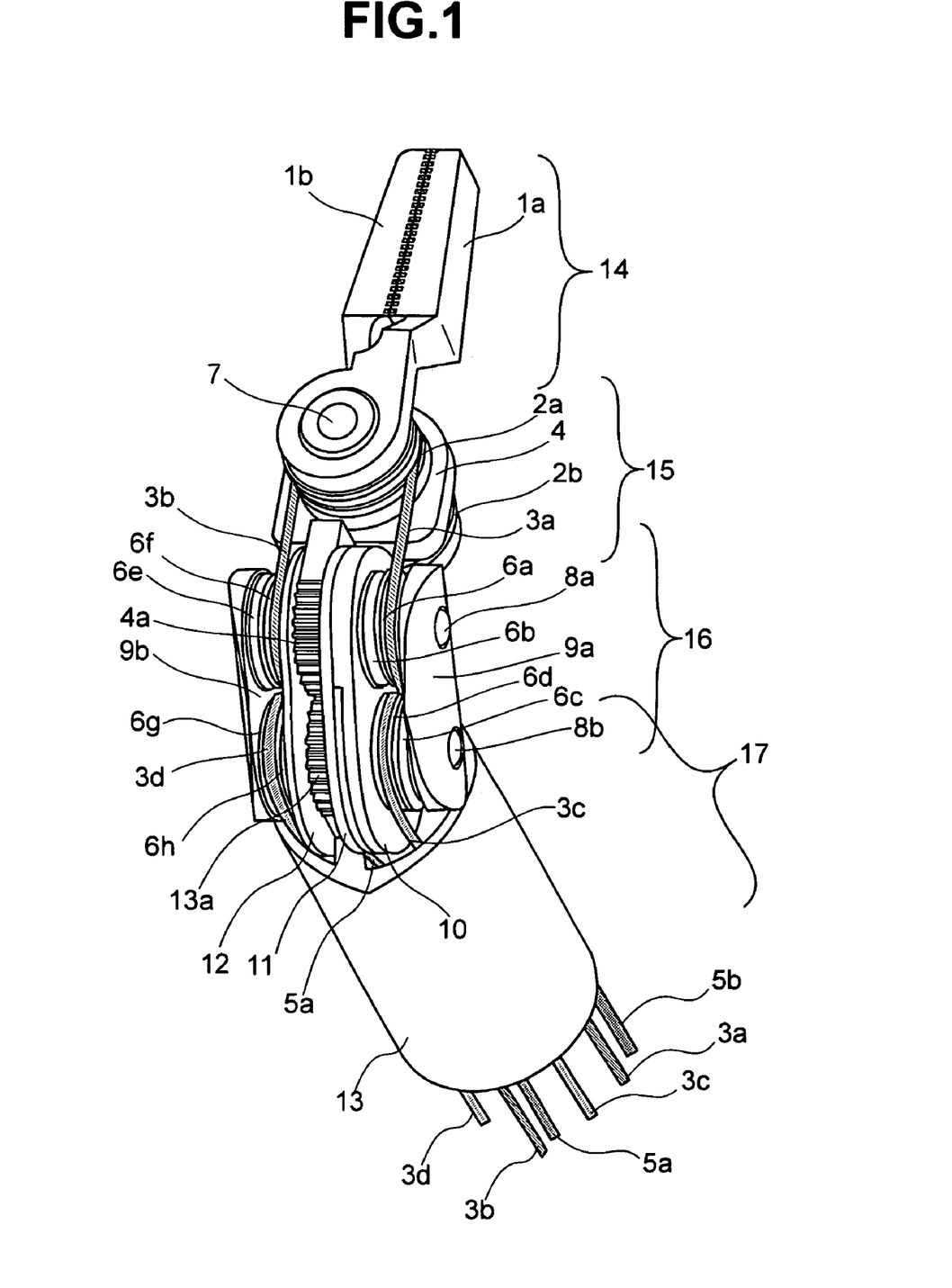
FIG. 1 is a perspective view of a manipulator, according to an embodiment of the present invention.
Figure 2:
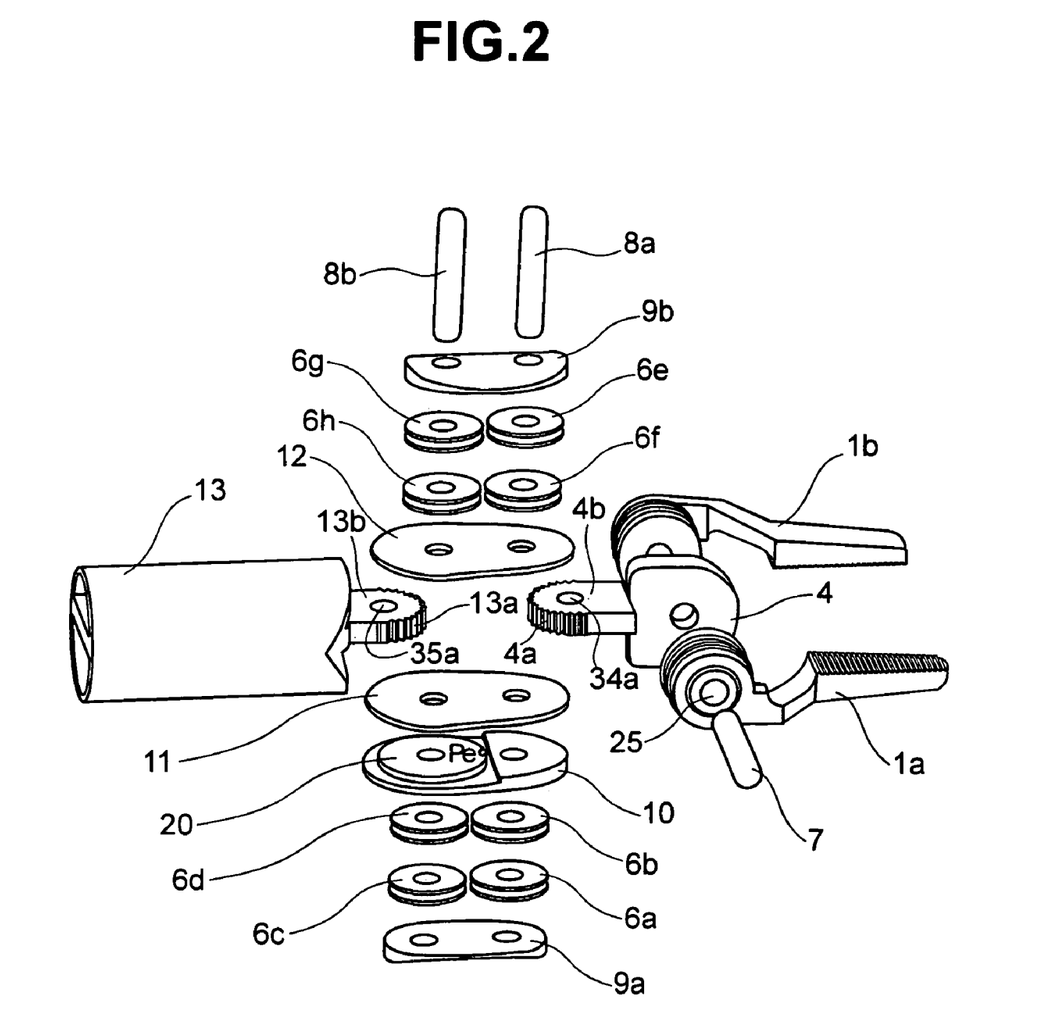
FIG. 2 is an exploded and perspective view of a joint portion, which is used in the manipulator shown in FIG. 1.
Figure 3:
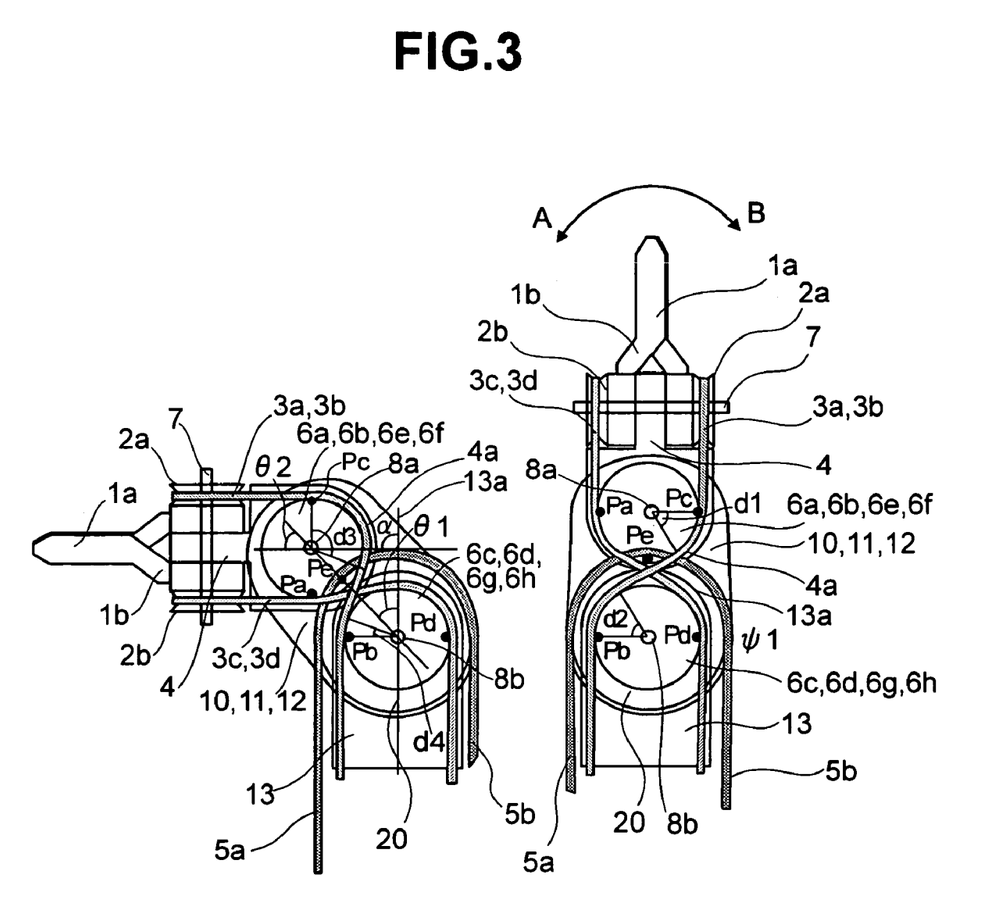
FIGS. 3(a) and 3(b) are views for explaining the wiring conditions of wires in the manipulator according to the present invention.
Figure 4:
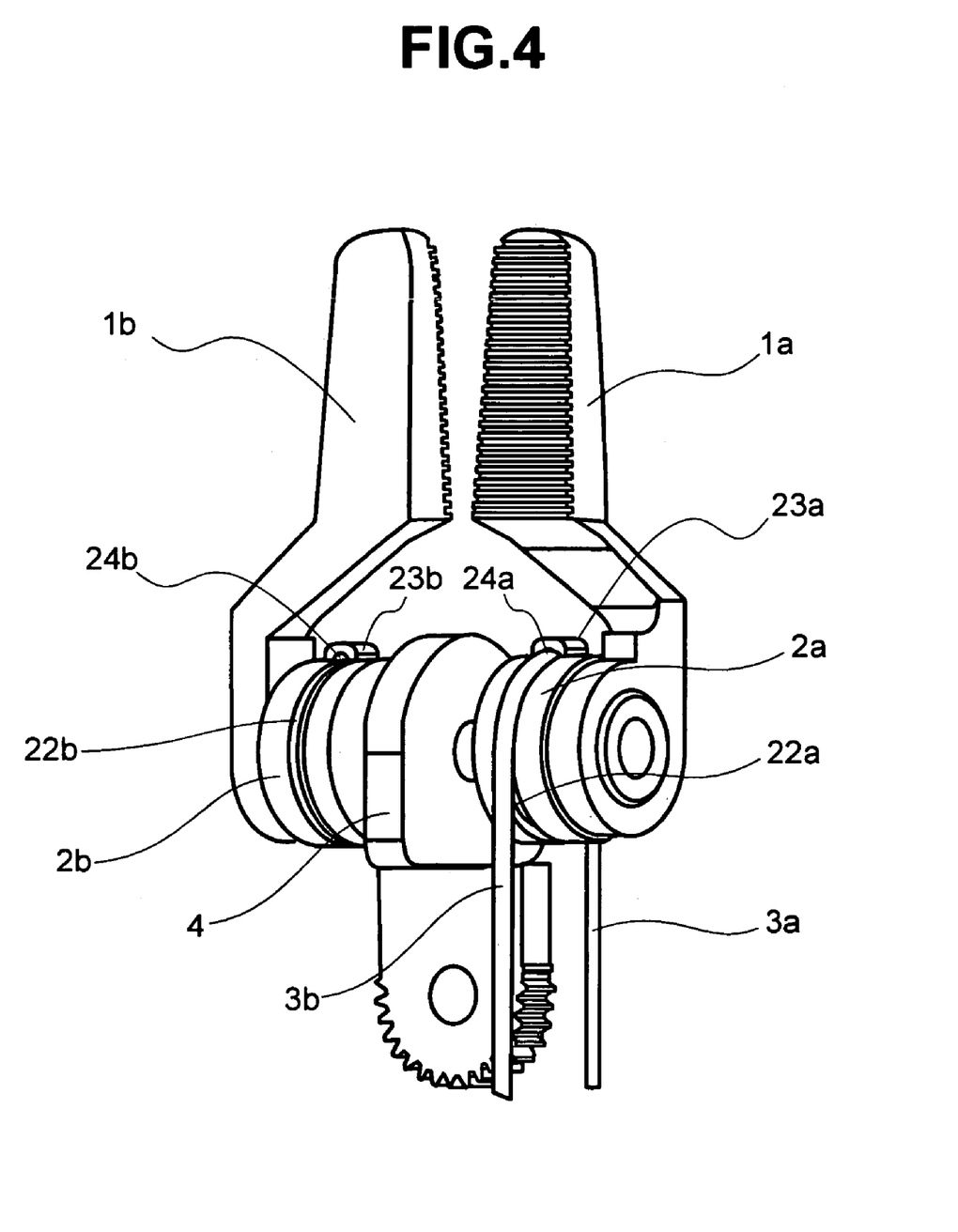
FIG. 4 is a detailed perspective view of a tip portion of the manipulator shown in FIG. 1.
Figure 8:
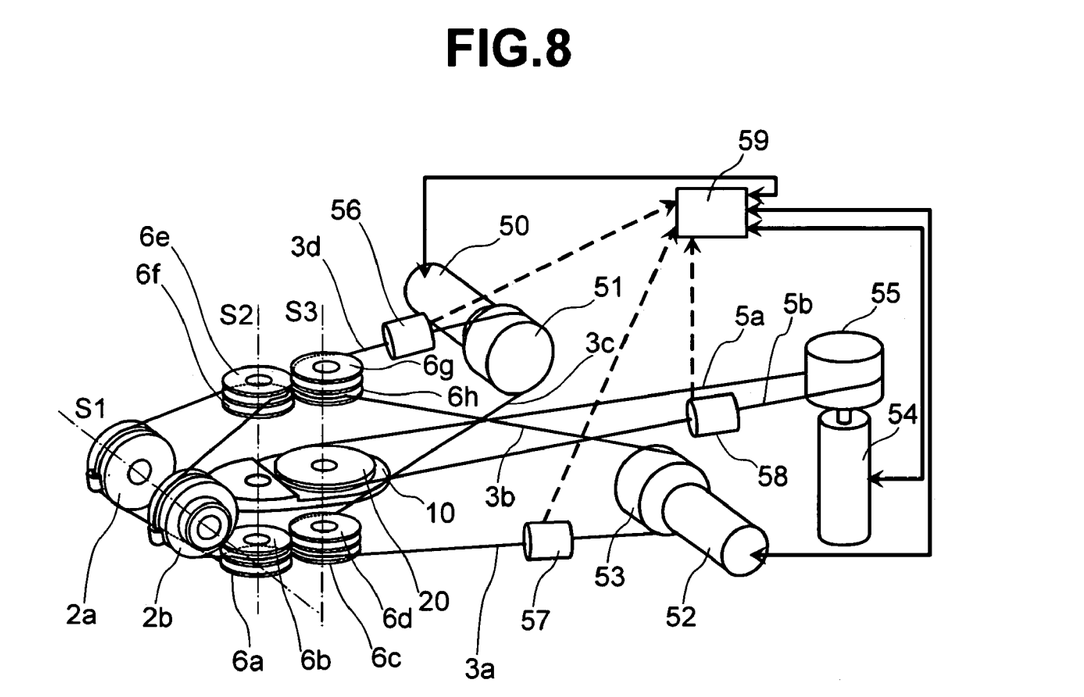
FIG. 8 is a view for explaining the wiring conditions of wires in the manipulator according to the present invention.

Hereinafter, embodiments according to the present invention will be fully explained by referring to the attached drawings. Herein, FIG. 1 is a perspective view of a tip portion of a manipulator, and FIG. 2 is an exploded and perspective view of a joint portion of the manipulator shown in FIG. 1. In FIG. 2, blades and wires for driving the oscillation thereof are omitted, for easy understanding. FIGS. 3(A) and 3(B) show the conditions where the joint is in straight and is bent, for explaining the wiring condition of wires. FIG. 4 is a detailed perspective view of a surgical tool at a tip portion of the manipulator, and FIG. 8 is a perspective view for explaining the wiring condition of wires at the actuator side.

With the embodiment, which will be mentioned hereinafter, explanation will be given on an example, in particular, a manipulator to be used for a medical or clinical purpose. The manipulator for medical use has a grip or hold portion 14 for gripping or holding a sewing thread and a needle, etc., a tip portion 15 located in the vicinity of a lower portion of the grip portion 14 in the figure, a middle portion 16 for making up a second joint together with the tip portion 15, and a base or root portion 17 for making up a first joint together with the middle portion 16. And, for operating the grip portion 14, the tip portion 15, and the middle portion 16, they also have wires such as, 3a to 3d, and 5a and 5b. On a side further lower side than the root portion 17, there is provided a driver/controller potion not shown in the figure, for controlling an each amount of pulling of the driving wires 3a to 3d, and 5a and 5b.

The grip portion 14 has a pair of blades 1a and 1b, and at the root portions of the blades 1a and 1b are positioned blade pulleys 2a and 2b, respectively. On the blade pulleys 2a and 2b are formed grooves 22a and 22b, on which the driving wires 3a to 3d are wound around for driving the blades, and also are formed holder portions 23a and 23b, for holding the wires 3a to 3d winding around those grooves 22a and 22b on the blade pulleys 2a and 2b.

The tip portion 15 has a plate-like tip base portion 4, put between the pair of blades 1a and 1b, and a rotating member 4b, being in a form of a plate crossing at about right angles with the tip base portion 4, and having a semicircular gear portion 4a. At a center portion of the tip base portion 4, a hole is formed, and a shaft 7 passes through this hole, as well as, holes formed in the center portion of the blade pulleys 2a and 2b. Also a hole is formed at the center portion of the gear portion 4a, and a shaft 8a passing through this hole penetrates through a hole formed in the middle portion 16. Further, the maximum width at a front side is 5 mm.

The root portion 17 has a cylindrical portion 13 and a rotating portion 13b located at a tip portion of the cylindrical portion 13 and formed a semicircular gear portion thereon. Also, a hole is formed at a center portion of the rotating member 13b.

Between the tip portion 15 and the root portion, the middle portion is formed, so that the tip portion 15 and the root portion 17 can rotate around on each of the two (2) pieces of shafts 8a and 8b. Namely, the middle portion 16 has egg-shaped middle plates 9b and 12, which are attached on the shafts 8a and 8b and are formed with two (2) pieces of the holes thereon. Pulleys 6e to 6h for guidance of wires, are put between those middle plates 9b and 12, egg-shaped middle plates 11 and 9a, which are also attached on the shafts 8a and 8b and are formed with two (2) pieces of the holes thereon. A middle plate 10 neighboring the middle plate 11, is formed with a disc-like convex portion 20 on a side, through which the shaft 8b passes. Pulleys 6a to 6d for use in guiding the wires, are put between the middle plate 10 and 9a.

The middle plate 10 is lowered around the convex portion 20 thereof. A periphery of the hole, through which the shaft 8a passes, is formed to be equal to the convex portion 20 in the height thereof. Connecting the plates 10 and 11, which are formed in this manner, makes up guide routes for the wires 5a and 5b. Between the plats 11 and 12 are put the rotating member 4b and 13b. The shafts 8a and 8b pass through the holes, which are formed in the plates 9a, 9b and 10 to 12 and the pulleys 6a to 6g. Each of the pulleys 6a to 6g is rotatable around the shaft 8a and 8b, and the rotating members 4b and 13b are in contact while rotating, in the gear portions 4a and 13a. Those members are made of a titanium alloy, for example, being light in weight and high in rigidity, as well as, protecting them from generation of rust or the like thereon.

FIG. 8 shows the condition of suspension of the wires. On a periphery of the convex portion 20 of the middle plate 10, and also at a crossing-point Pe connecting between the middle portions of the two (2) pieces of the shafts 8a and 8b, as well, the wires 5a and 5b are fixed and are wound around an outer periphery portion of the convex portion 20. Passing through an inside of the cylindrical portion 13, those wires 5a and 5b are suspended around a pulley 55, which is attached on an end of the shaft of an oscillation or swing motor 54, and reach to one (1) point on an outer periphery of the pulley 55. In a middle or on a portion of the wire 5b, a tension detecting means 58 is attached. The wires 5a and 5b may be one (1) piece of continuous wire, or may be two (2) separate pieces of wires.

As is shown in FIG. 4, grooves are provided on the blade pulleys 2a and 2b, for suspending the wires thereon. Wire fixing portions 23a and 23b are attached on the pulleys 2a and 2b, in an outer periphery part thereof. A portion of the wire 3a or 3b is fixed at the fixing portion 23a or 23b, such as, though bonding, welding, blazing, or caulking, etc., for example.

As is shown in FIG. 8, the wire 3a is fixed at the one (1) point on the blade pulley 2a and is guided to the pulley 6a and next to the pulley 6c. Thereafter it is fixed at the one (1) point on the outer periphery of a motor pulley 53, which is provided on the shaft end of a blade driver motor 52. In a similar manner, the wire 3b fixed at the one (1) point on the pulley 2b is guided to the pulley 6f and then, next to the pulley 6h. The wire 3b is also fixed at one (1) point on the outer periphery of the motor pulley 53, which is attached at the shaft end of the blade driver motor 52. In a middle of the wire 3a is provided a tension detecting means 57. Though the wire 3a and the wire 3b are mentioned to be one (1) continuous piece of wire in the present embodiment, they may be two (2) pieces of wires, which are fixed on the blade pulleys 2a and 2b.

Also, on a side of the blade 1b, the wires 3c and 3d are suspended in the similar manner to the side of the blade 1a. Thus, the wire 3c fixed at the one (1) point on the blade pulley 2b is guided to the pulley 6b, and next to the pulley 6d. In this instance, although the wire 3c comes across between the pulleys 6b and 6d from a direction crossing the wire 3a, however since the wire 3a and the wire 3c are made different in the height of the pulleys, on which the wire 3a and the wire 3c are suspended, therefore those wires will not contact each other.

The wire 3c is guided from the pulley 6d to the motor pulley 51, which is attached to the blade driver motor 50, and is fixed at one (1) point of the outer periphery of a motor pulley 51. The wire 3d fixed at one (1) point on the blade pulley 2b is guided to the pulleys 6e and 6g. Since the pulleys 6e and 6g and the pulleys 6g and 6h are made different in height, the wire 3d will not contact the wire 3b. The wire 3d is guided from the pulley 6g to the motor pulley 51 attached to the blade driver motor 50, and it is fixed at one (1) point on the outer periphery of the motor pulley 51. In a middle of the wire 3d is provided a tension detecting means 56.

Explanation will be given on an operation of the manipulator, being constructed in this manner, according to the present invention. The grip portion 14 rotates around the shaft 7 with respect to the tip portion 15. In this instance, if the shaft 7 and the blades 1a and 1b in the same direction of rotation, the grip portion 14 changes the direction thereof. On the other hand, if the blades 1a and 1b rotate in the reverse direction of the shaft 7, the grip portion 14 performs an operation to open/close. In more details, when driving the blade driver motor 52, for rotating the motor pulley 53 to thereby pull up the wire 3b, the blade 1a moves in the direction of closing. On the contrary, if pulling up the wire 3a, the blade 1a moves in the direction of opening. When driving the blade driver motor 50, for rotating the motor pulley 51, thereby to pull up the wire 3c, the blade 1b is closed, while it is opened if pulling up the wire 3d. If pulling up together the wires 3a and 3c, or the wires 3b and 3d, then the grip portion rotates around the shaft 7, thereby changing the direction of grip. This is called by the oscillation or swing of the joint of grip portion.

An angle α of the oscillation or swing angle of the tip portion can be expressed by the sum of an angle θ1, which is defined by the root portion 17 and the middle portion 16, and an angle θ2, which is defined by the middle portion 16 and the tip portion 15. When driving the oscillator motor 54, for rotating the motor pulley, thereby pulling up the wire 5a, then the middle plate 10 rotates in a direction A in FIGS. 3(a) and 3(b) around the shaft 8b. At the same time, also the tip portion 4, the pulleys 6a, 6b, 6e and 6f, and middle plates 9a and 9b rotates in the direction A in FIGS. 3(a) and (b), but around the shaft 8b. In this instance, the gear portions 4a and 13a perform a meshing operation while being in contact and rotating.

If the gear portion 4a and the gear portion 13 are the same size, the tip portion 15 is rotated by the angle θ1 around the shaft 8b when the middle plate 10 rotates by the angle θ1 around the shaft 8b, and accompanying this, it also rotates by the angle θ2=θ1, around the shaft 8a. With this, the angle α of oscillation or swing of the tip portion 15 to the base portion 17 comes to be as two (2) times as large as the angle of rotation of the middle plate 10 around the shaft 8b. When driving the driver motor 54 for rotating the motor pulley 55, thereby pulling up the wire 5b, the tip portion 14 oscillates or swings in a direction B as shown in FIGS. 3(a) and 3(b). Also in this instance, being similar to the oscillation in the direction A, the angle α of oscillation or swing of the tip portion 15 to the base portion 17 comes to be as two (2) times as large as the angle of rotation of the middle plate 10 around the shaft 8b.

In a case where a radius of the gear portion 4a is R times large as that of the gear portion 13a, the tip portion 15 rotates by an angle θ2=θ1/R around the shaft 8a when the middle plate 10 rotates around the shaft 8b by the angle of θ1. Accordingly, the tip portion oscillates or swings by an angle α=θ1(1+1/R) to the root portion 17.

The central angle of a pulley, in the portion where the wires 3a and 3b is in contact with each of the pulleys, changes depending upon the oscillation or swing angle α. For example, the wire is in contact with two (2) pieces of the pulleys 6a and 6c. The sum of the central angles of the portions where the wire 3 is in contact with those two (2) pulleys 6a and 6c is d1+d2 in FIG. 3(a), but is d3+d4 in FIG. 3(b). Those values are always contact since the gear portions 4a and 13 are in contact with each other while meshing or engaging to each other, therefore they are not dependent upon the oscillation or swing angle α of the joint of tip portion which is defined by the root portion 17 and the tip portion 15. Accordingly, the route length of the wire between points Pa and Pd and that between the points Pc and Pb are not variable (always constant) independent upon the angle α, and no change occurs in the phases of the wires.

Herein, the phases of wires are the open/close angles of the blades 1a and 1b, however they also relate to the positions of the wires depending upon the open/close angles. In other words, they correspond to an amount of pulling of the wires by the driver portion. Since no change occurs in the phases of the wires, the blades 1a and 1b will not open/close even if the joint of the tip portion 14 moves. With this, if the angle α changes at the joint of the tip portion 14, no influence is given on the wires, which controls the blades 1a and 1b provided at further end of this joint, in particular, on the route length, the phases and the tensions thereof. As a result, the tension detecting means 56, 57 and 58 are able to detect only the tension needed for driving the movable portions. Since the operation of each joint is independent, the tension detecting means 56 measures the rotation torque of the blade 1a, independently. Also, the tension detecting means 57 measures the rotation torque of the blade 1b independently, and the tension detecting means 58 measures the rotation torque of the convex portion 20 independently. Each of the motors 50, 52 and 54 is controlled by means of a controller apparatus 59. Further, the tensions detected through the tension detecting means 55 to 57 are inputted into the controller apparatus 59.

According to the present embodiment, since the open/close angle of the blades 1a and 1b can be held constant by operating the wires 5a and 5b when performing the oscillating or swing operation, there is no need for controlling the amount of pulling of the wires 3a to 3d. Also, since no change occurs in the route length of the wires even if the oscillating or swing angle is changed, it is possible to prevent such a situation from occurring where no change can be obtained because the wires have been already pulled up. Also, no such situation occurs where the wires are loosed when the oscillating or swing angle is changed, it is possible to prevent the wires of the driver portion from running idle up to when obtaining a certain tension necessary for operating the blades. With this, there is no necessity for the actuator to change the position thereof, even when it performs the oscillating or swing operation and/or the opening/closing operation.

According to the present embodiment, there is no need to adjust the wire length by equipting two (2) pieces of the actuators for each one (1) of the degrees of freedom; therefore it is sufficient that the number of pieces of the actuators is same to the number of the degrees of freedom. Since one (1) piece of the actuator is used for each one (1) degree of freedom, the joint comes to be smooth in operation, thereby obtaining a stable operation. Also, since the tension can be captured correctly, it is possible to grip or hold an object with an appropriate force, such as, when sewing or stitching vessels and/or tissues in an actual field of medical treatment, for example. With this, it is possible to conduct a treatment of low attacking.

Since the wires for oscillating or swing and the wires for opening/closing the grip portion can be controlled independently, control comes to be easy, as well as being stable in operation. The opening/closing operation of the blades can be performed at an arbitrary angle of oscillation or swing within a movable region thereof. Also, the operation of oscillation or swing while gripping or holding an object by the blades, can be performed with accuracy. Also, because of the provision of the middle portion 16 having the two (2) pieces of rotation centers, it is possible to widen the region where the tip portion 15 can oscillate or swing to the root portion 17. For this reason, it is possible to make a treatment on the seat of a disease portion which is hidden behind an organ, using the manipulator.

Figure 5:
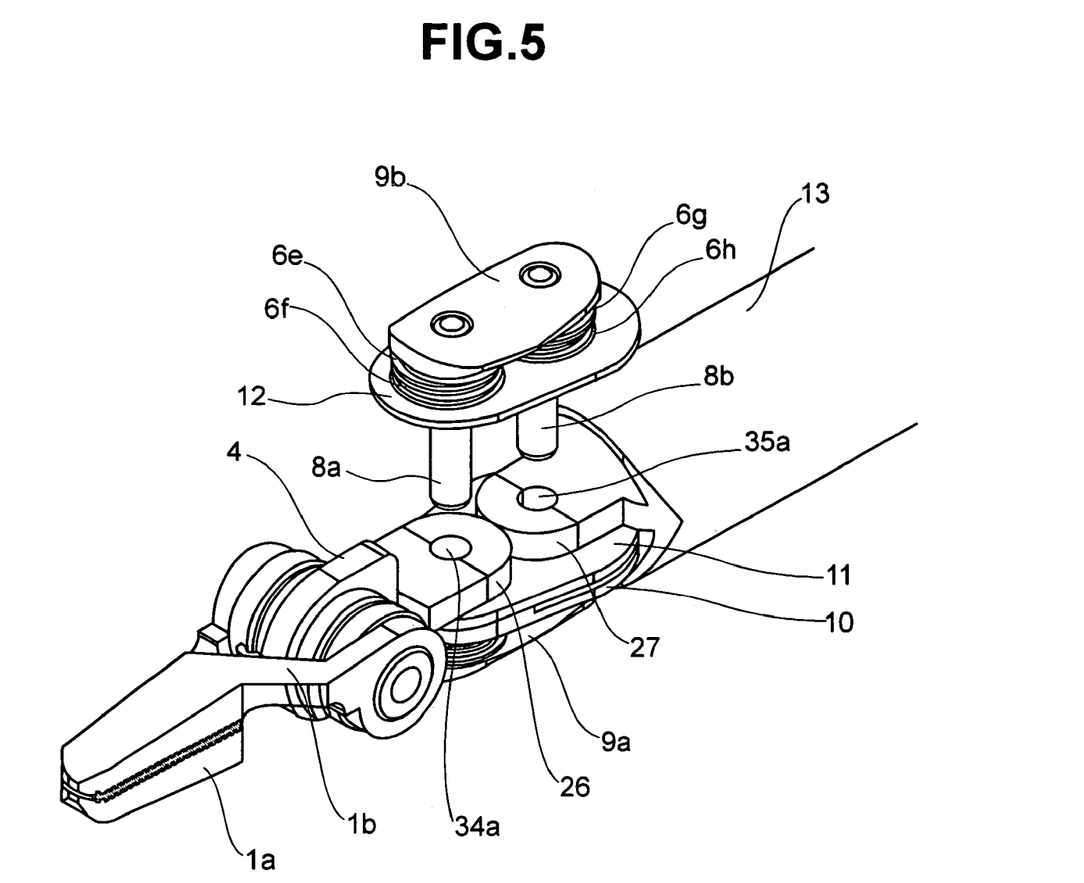
FIG. 5 is a perspective view of a variation of the manipulator according to the present invention.

A variation of the manipulator, according to the present invention, will be explained, by referring to FIG. 5. In the present embodiment, rotating members 26 and 27 are used, each having a semicircular portion on a surface of which hard surface treatment is conducted, in the place of the rotating members 4b and 13b having the gear portions 4a and 13a, thus differing from the embodiment mentioned above. The rotating members 26 and 27 have surfaces to be in contact with each other, on which the coefficient of static friction is increased through roughening the surfaces. Those rotating members 26 and 27 are formed with holes 34a and 35a, at the rotation center thereof, and the shafts 8a and 8b are inserted in those holes. Those rotating members 26 and 27, in particular, are kept at a constant distance between the rotating centers thereof.

According to the present variation, it is possible to rotate the rotating members, due to the static friction, which occurs at contact points. For increasing the coefficient of static friction, they may be treated with, for example, a surface treatment for increasing the surface roughness, or a surface treatment with a film or the like having high viscosity and/or having high adherence, or a surface treatment of film of high hardness. Also, it is possible to reduce looseness due to back-lash, compared to the embodiment mentioned above.

Figure 6:
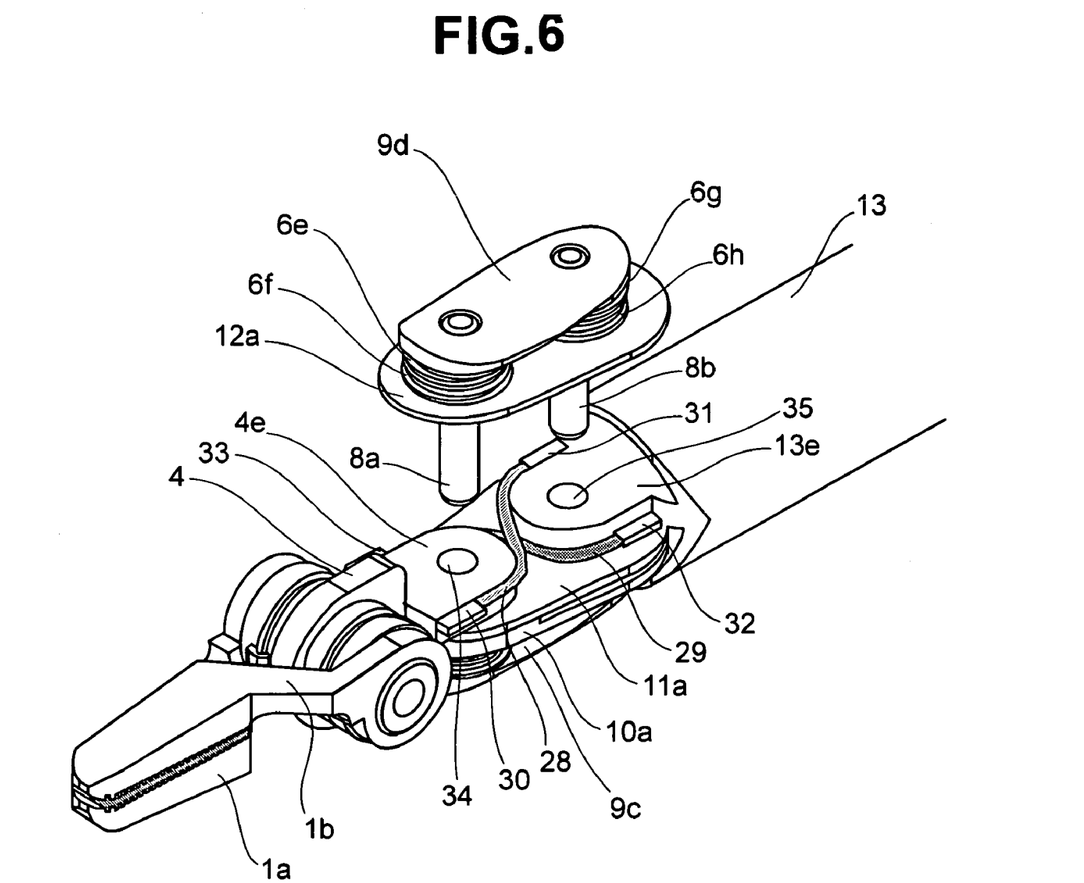
FIG. 6 is also a perspective view, but of another variation of the manipulator according to the present invention.

Other variation of the present invention will be explained by referring to FIG. 6. In the present variation, there are used rotating members 4e and 13e, each having a semi-circular portion; and two (2) pieces of string-like members 28 and 29, each fixed at and end portion thereof on the respective rotating members 4e and 13e, in place of the rotating members 4b and 13b. The end portions of the string-like members 28 and 29 are fixed at fixing portions 31 to 33 on side surfaces of the rotating members 4e and 13e. Those two (2) pieces of string-like members 28 and 29 are belted crossing with each other, and are fixed at the fixing portions 31 to 33 without loosing or stretching. However, a gap is formed a little bit between the rotating members 4e and 13e.

According to the present variation, the tip portion 15 and the root portion 17 can rotate without sliding in the middle portion 16. Since the shifting thereof can be restricted physically in the direction of sliding, it is therefore possible to control the rotation angle with ease. Namely, according to the present variation, it is possible to obtain an effect, being equal to those of meshing of gears and rotating contacts. Also, comparing to the meshing of gears, it is possible to make small the backlash thereof, thereby enabling to loosen a common difference or tolerance between the shafts 8a and 8b, compared to the case where they are in contact while rotating.

Figure 7:
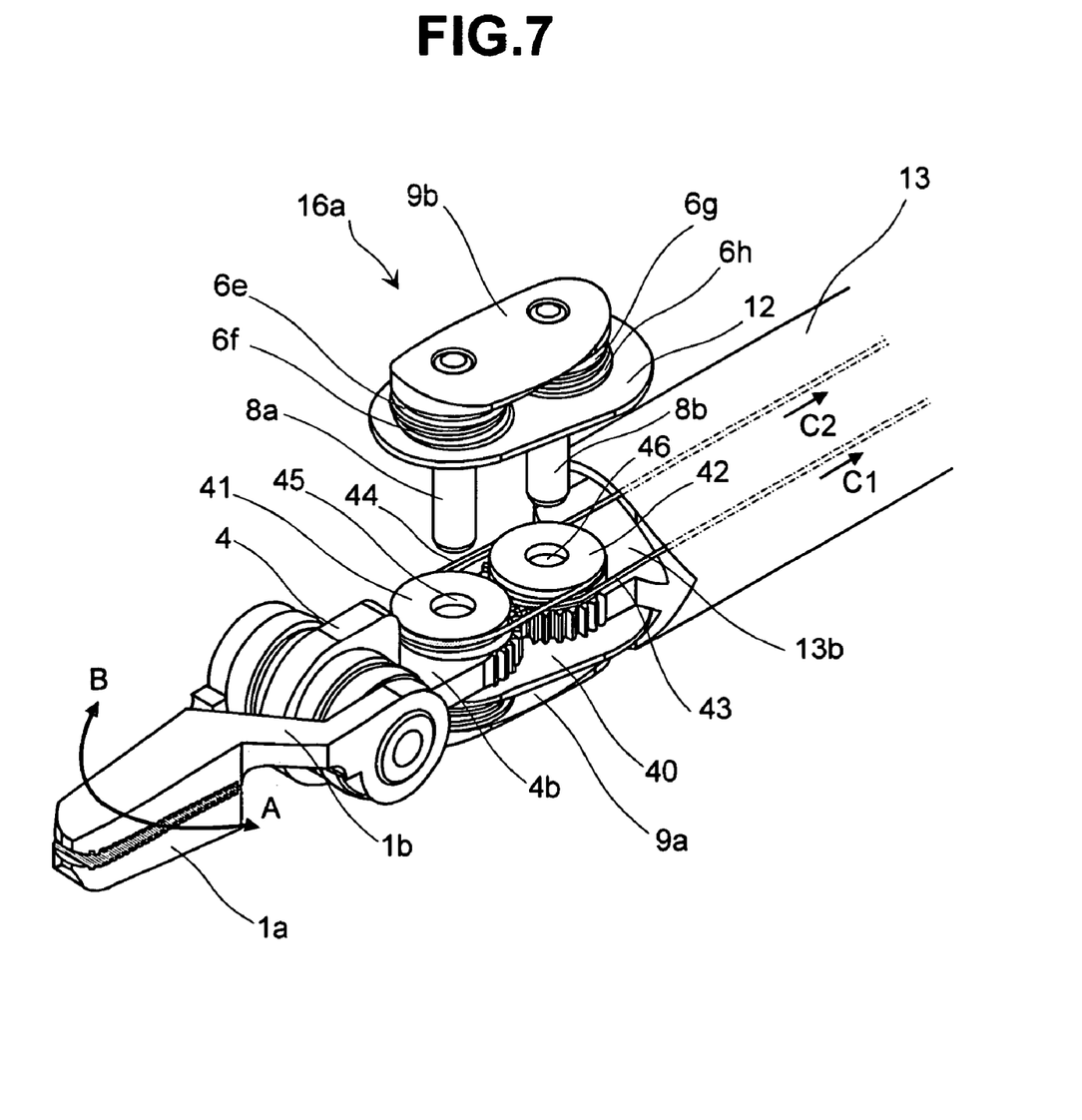
FIG. 7 is also a perspective view of a further variation of the manipulator according to the present invention.

Further other variation of the manipulator according to the present invention will be explained, by referring to FIG. 7. With the present variation, pulleys 41 and 42 having central bores 45 and 46 are disposed, between the rotating members 4b and 13b, building up the middle portion 16a, and the middle plate 12, wherein a wire 44 is attached via those pulleys 41 and 42. And, the middle plate 10 that is shown in FIG. 1 is omitted therefrom. However, in the present variation, the pulley 41 is formed with the rotating member 4b in one body, while the pulley 42 with the rotating member 13b.

Further, two (2) stages of grooves are formed upper and lower on the pulley 42 at the root side, and a wire 43 is wound around in the groove of the upper stage side. This wire 43 is fixed at one (1) point on an outer periphery portion of the pulley 42. Into the groove on the lower stage side of the pulley 42, the wire 44 mentioned above is wound around. The wire 44 is fixed at one (1) point of the outer periphery portion of the pulley, e.g., either one of the pulleys 41 or 42.

With the present variation, being constructed in this manner, the pulley 42 rotates in a direction C1 on the shaft 8 when the wire 43 is pulled up in a direction C1. This rotation is transmitted through the wire 44 to the tip pulley 41. As a result, the rotating member 4b rotates around the shaft 8a. Since the rotating members 4b and 13b are meshed to the gear portions 4a and 13a, the middle portion 16a rotates around the shaft 8b with respect to the cylinder portion 13. When the wire 43 is pulled up in a direction of C2, the middle portion 61a perform the operation of oscillating or swinging to a direction B.

Also, according to the present variation, it is possible to make the tip joint conducting the oscillation or swing operation, in the similar manner as in the embodiment of each of the variations mentioned above. The rotating member may be one of the following, other than that having the gear portion thereon: a member having a predetermined surface roughness, a member having increased viscosity or adhesiveness, or one having a means for suppressing sliding within an plane operation surface thereof. Further, if it is in such a structure that the grip portion and the tip portion come across at 90 degree in the oscillation or swing direction, it is possible for the wires 3a to 3d controlling the blades 1a and 1b to share or function as the means for suppressing the sliding with each other.

For oscillating or swinging the tip portion, it is also possible to provide a motor at any one of the tip portion, the middle portion and the root portion, as well as, a link, for example, in the place of using the driving wires. Also, in the present variation, when wiring the wires or the wire-like flexible members for driving the joint located at the tip side through the joint at the root side, it is possible to compensate the route lengths and the phases thereof.

Figure 9:
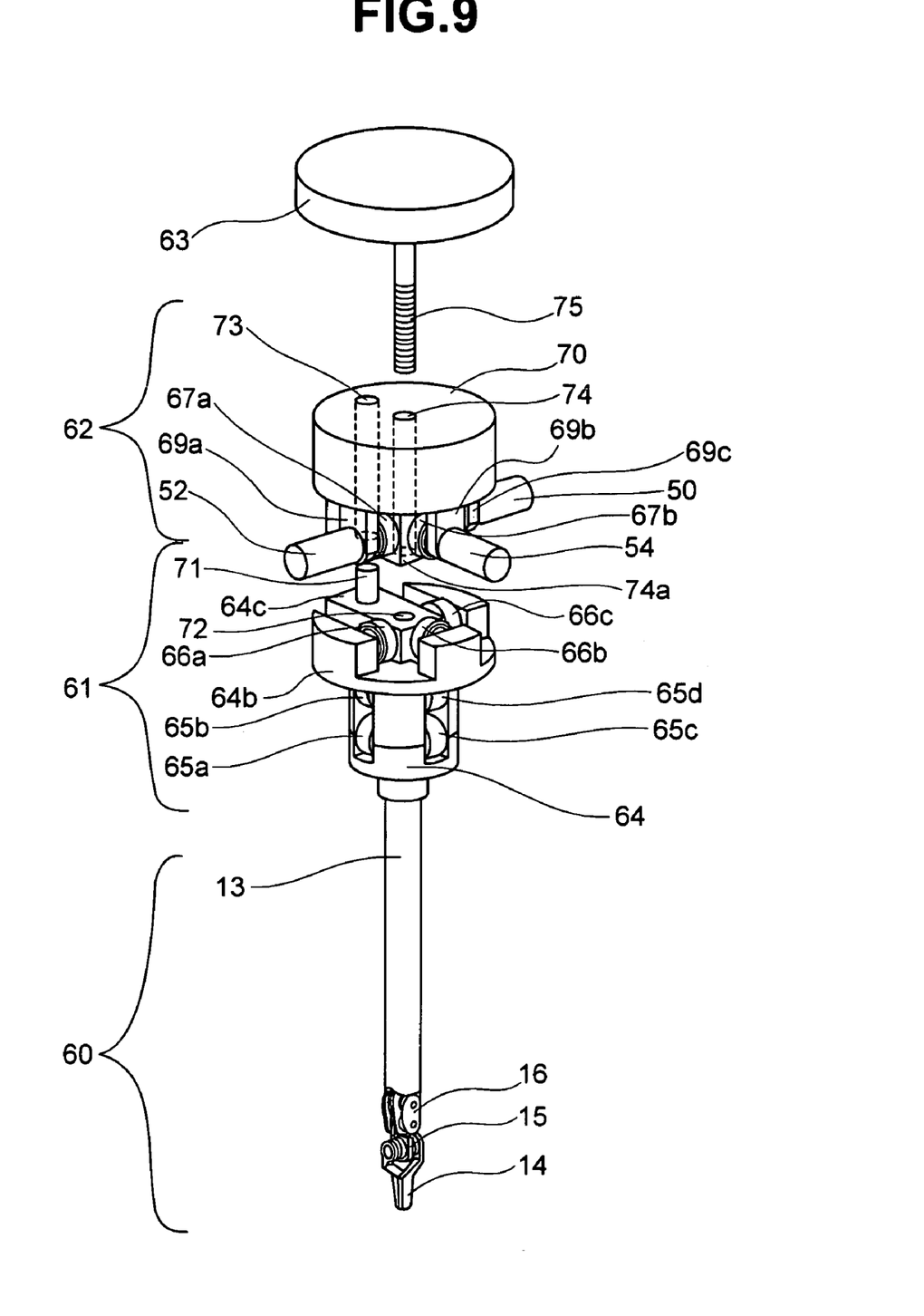
FIG. 9 is a perspective view for showing a manipulator, according to another embodiment of the present invention.
Figure 10:
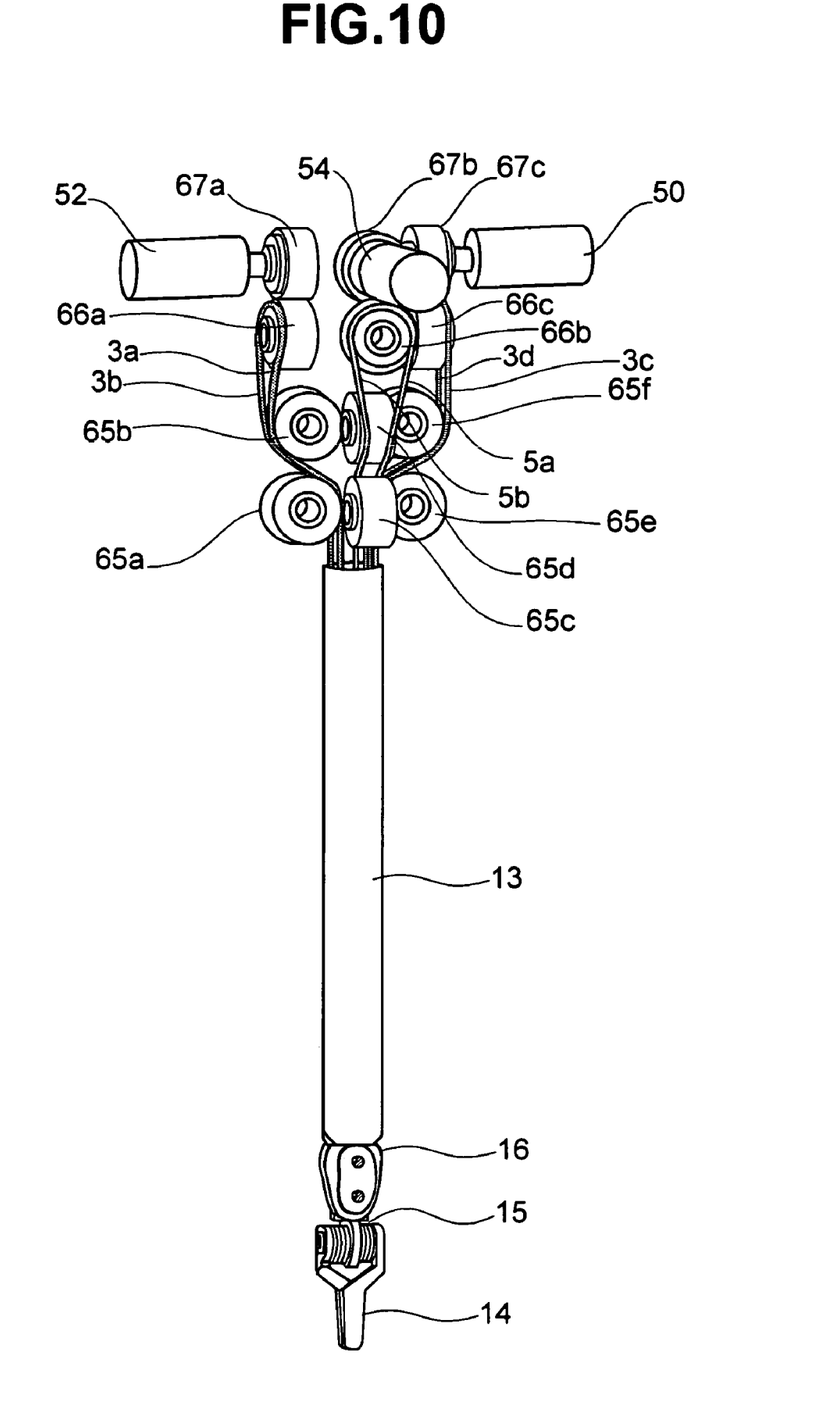
FIG. 10 is a view for explaining the wiring conditions of wires shown in FIG. 9.

By referring to FIGS. 9 and 10, explanation will be given on a manipulator, according to another embodiment of the present invention. FIG. 9 is a perspective view of the manipulator, and FIG. 10 is a perspective view for explaining the wiring condition of wires in a dividing mechanism shown in FIG. 9. In the present embodiment, other than those from the tip portion of the manipulator 14 to the cylinder portion 13, there are further included a connection portion 61 of a surgical equipment or tool, a driver portion 62 and a fixing screw 63. With the present embodiment, the surgical equipment or tool and the driver potion can be separated from each other.

The surgical tool portion 60 has the grip portion 14, a tip portion, the middle portion 16 and the cylinder portion 13. The surgical tool portion 60 can be in the form described in the embodiment and the variations mentioned above. The surgical tool connection portion 61 has a cylinder-shaped case portion 64 and a column-like base portion 64b, having a diameter larger than that of the case portion 64. Within the case portion 64 is stored rollers 65a to 65f, and an outer periphery side thereof are formed with cutting portions at a plural number of positions for suspending the wires thereon, which will be mentioned later.

On the base portion 64b is formed a groove portion which has a hollow central portion. A block 64c, on which the rollers 66a to 66c are attached covering an upper portion of the hollow portion, is attached in the groove portion. On one side of the rollers 66a to 66d, grooves are formed for suspending the wires 3a to 3d, 5a and 5d thereon. The diameter of those grooves is smaller than that of the rollers even after being suspended with the 3a to 3d, 5a and 5d therein. In the block 64c, a screw hole 72 is formed for fixing the driver portion 62 by means of a fixing screw 63. On an upper surface side of the block 64c, a pin 71 is attached for use of positioning when fixing the driver portion 62 to the surgical tool connection portion 61.

The driver portion 62 has a driver base portion 70, a positioning portion 70a projecting into a lower surface side of the driver base portion 70 in a rectangular shape, and fixing portions 69a to 69c for three (3) motors. On the positioning portion 70a, a hole 73 for inserting the pin 71 of the surgical tool connection portion 61 and a hole 74 for use of the fixing screw 63, are formed penetrating up to the driver base portion 70. The height of the positioning portion 70a is determined such that the roller 66a to 66c are in contact with the roller 67a to 67c while rotating when the rollers 67a to 67c are attached at the shaft ends of the respective motors 50, 52 and 54. Further, in place of the roller 66a to 66c and 67a to 67c, it is also possible to use gears engaging each other.

As is shown in FIG. 10, the wires 3a to 3d, 5a and 5d guided from the cylinder portion 13 are suspended into the groove portions formed on the rollers 66a to 66c, using the rollers 65a to 65f as guides. Since those rollers 66a to 66c are in rolling contact with the roller 67a to 67c, then the driving forces from the motors 50, 52 and 54 are transmitted to the wires 3a to 3d, 5a and 5b, thereby the amount of pulling of each of the wires 3a to 3d, 5a and 5b is controlled.

With the present embodiment, since having three (3) wire driving systems, each being able to drive the joint operation independently, there is no interference with one another, nor necessity of compensating an ill influence due to the mutual operations thereof. As a result, the joint mechanism can be simplified. Also, there are provided only the driver motor and the rollers or gears attached to the motor, in the driver potion 62; i.e., the wire is not guided up to the driver portion, thus the surgical equipment or tool can be easily separated or divided from the driver portion by removing the fixing screw from the connection thereof. Further, the surgical equipment or tool can easily be connected to the driver portion only through positioning while fitting or inserting the pin 71 into the hole 73, and fixing them by means of the fixing screw 63, therefore various surgical equipments or tools can be quickly exchanged.

According to the present embodiment, it is possible to connect or separate the driver portion and the surgical equipment or tool, with a simple structure thereof, thereby obtaining small sizing, light weighting and simplification of the separation mechanism. As a result, it is possible to improve the manipulator's reliability and safety. Also, there is no need for complex adjustments; therefore, the manipulator can be superior in a characteristic of maintenance, and able to is reduce a possibility of generating the accident and/or drawback therein. With enabling the small sizing and the light weighting thereof, it is possible to provide a manipulator and surgical tool, that is superior in operability, as well as in the manufacturing cost.

Figure 11:
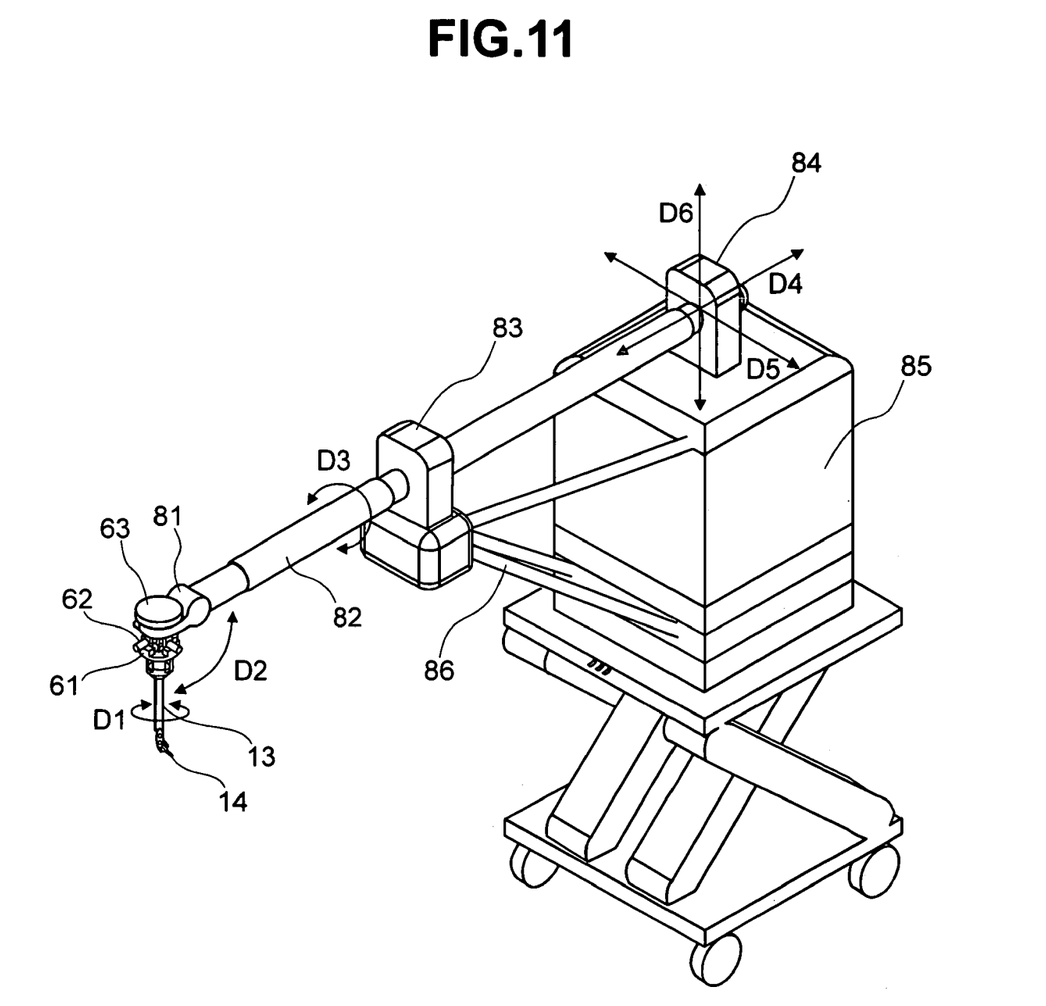
FIG. 11 is a perspective view of an embodiment of a manipulator system using therein the manipulator according to the present invention.

FIG. 11 is a perspective view showing an example of a manipulator system using a manipulator such as those shown in the embodiments mentioned above.

The manipulator system has a manipulator main body 85 and an arm 82, on which the main body 85 is attached. It is constructed such that the surgical tool 60 can be attached onto the arm 82, by putting a surgical tool attachment joint 81 between the fixing screw 63 and the driver portion 62 of the manipulator shown in FIG. 9.

On a middle portion of the shaft direction of the arm 82 and on an opposite end of the surgical tool attachment joint 81, there are provided gimbal portions 84 and 83. The gimbal portion in the middle of the arm 82 is fixed on the main body 85 by means of a holding arm 86. The gimbal portion 84 on the end side of the arm 82 is structured such that the arm can move in directions D4 to D6 parallel with the main body 85. Also, the gimbal portion 83 in the middle of the arm 82 is movable in a direction D3 rotating around the shaft of the arm 82.

When the gimbal portion 84 at the end of the arm 82 operates, the arm 82 moves the surgical tool attachment joint 81 at the tip of the arm 82 by using the gimbal portion 83 as a fulcrum. In this instance, it is moved in the direction D4; e.g., the gimbal 84 and the surgical tool attachment joint 81 are moved together along the axial direction of the arm. With the two (2) directions D5 and D6, being orthogonal to the shaft of the arm 82, the gimbal portion 84 and the surgical tool attachment joint 81 operate in the reverse direction around the gimbal portion 83. When rotating the arm 82 around the shaft (i.e., in the direction D3), the surgical tool attachment joint 81 rotates in the direction orthogonal to the shaft of the arm 82 (i.e., in the direction D2). This is the oscillation or swing operation of the surgical tool 60. Further, the surgical tool attachment joint 81 has a mechanism for rotating the surgical tool 60 around the shaft of the cylinder portion 14 (i.e., in the direction D1). The rotation of the manipulator in each of those directions D1 to D3 is controlled through the actuator and the controller apparatus, which are built in the main body 85 of manipulator or the arm 82, but not shown in the figure.

According to the present embodiment, since the manipulator can be moved in each of the directions D1 to D3 without interference, control of the manipulator system can be simplified. Further, with controlling the manipulator arm in six (6) degrees of freedom in addition to a plural number of degrees of freedom of the surgical equipment portion, it is possible to perform a complex medical operation.

In the embodiment mentioned above, though the explanation was given on the manipulator system, being continuous on the degree of freedom in the different directions, the present invention can be also applied to a manipulator system continuous on the degrees of freedom in the same direction. Also, though giving the explanation by taking a forceps, as an example of the grip portion, various effectors and medical tools also can be used, other than the forceps. Namely, if controlling the degree(s) of freedom through the side of the base portion, a similar effect can be obtained, to that of the various embodiments mentioned above. Also, other than the surgical tool, it can be applied to joints of a shoulder, a wrist, a finger, a knee and an ankle of a robot, or an articulated master-slave manipulator, etc.

Further, though omitting description about lines for detection signals and for electric power in the embodiments mentioned above, if wiring those in the similar manner to the routes of the wires, there is no need for loosing in excess at the joint portions. Also, it is possible to prevent the signal lines and the power lines from being picked up or wound around in the joint portions thereof. Further, when attaching a sensor using an optical fiber, or an observing means, such as, a soft type endoscope, etc., at the tip of a robot, if wiring or lying the fibers along with the wiring route of the wires, no external power is applied in excess onto the fibers nor the soft-type endoscopes; therefore a stable image can be obtained therefrom, and the endoscopes and the fibers can be improved on the lifetime thereof.

According to the respective embodiments and the variations mentioned above, since one of the two (2) pieces rotating members provided in the middle portion only revolute around the other, the relative positions between the actuators will not change, thereby making the control thereof easy. Also, the complex operation can be executed with the structure, being similar to a hand of a human; therefore a treatment can be made at positions where an approach is difficult.

As was fully explained in the above, according to the present invention, since the driving wires are suspended on the neighboring pulleys building up the joint portion for the manipulator, it is possible to maintain the route length and the phase of the driving wires constant, in spite of change in an angle of the joint, thereby enabling small-sizing of the manipulator, as well as, improving the controllability thereof.

The present invention may be embodied in other specific forms without departing from the spirit or essential feature or characteristics thereof. The present embodiment(s) is/are therefore to be considered in all respects as illustrative and not restrictive, the scope of the invention being indicated by the appended claims rather than by the forgoing description and range of equivalency of the claims are therefore to be embraced therein.

What is claimed is:

1. A manipulator having a plural number of joints therein, wherein at least one joint of the joints comprises:
    two rotating members, disposed in opposing relation to each other;
    a driving means for driving one of said rotating members to cause a rotating movement to the other rotating member;
    said driving means including a guiding means attached on a rotational shaft of each of said rotating members, and a first wire having at least one end thereof fixed to said guiding means; and
    a means for keeping a distance between rotational centers of said two rotating members constant,
    wherein said joint is a second or subsequent joint from a tip of the manipulator, and a second wire for driving a first joint located nearer to said tip portion is guided to said first joint on a side of the tip portion, passing through said guiding means of said second or subsequent joint, and
    wherein each of the rotating members has a semicircular shape and is integrally formed with a tip of one of a base portion of the manipulator and a cylindrical portion of the manipulator.

2. A manipulator, as described in the claim 1, wherein a tension detecting means is provided in a middle of said second wire.

3. A manipulator having a plural number of joints therein, wherein at least in one of said joints comprises:
    two rotating members, disposed in opposing relation to each other;
    a driving means for driving one of said rotating members to cause a rotating movement to the other rotating member;
    a means for keeping a distance between rotational centers of said two rotating members constant;
    a surgical tool portion;
    a grip portion provided on said surgical tool portion;
    a driver portion for driving said grip portion provided on said surgical tool portion, and
    a member for maintaining the length and phase of guiding wires used by the driver portion for driving the grip portion constant; wherein
    a surgical tool connection portion is provided between said surgical tool portion and said driver portion, and said surgical tool portion can be separated from or connected to, said driver portion and said surgical tool connection portion.

4. A manipulator, comprising:
    a surgical tool portion;
    a grip portion provided on said surgical tool portion; and
    a driver portion for driving said grip portion provided on said surgical tool portion, wherein
    a surgical tool connection portion is provided between said surgical tool portion and said driver portion, and said surgical tool portion can be separated from or connected to, said driver portion and said surgical tool connection portion;

wherein said surgical tool connection portion has a pin extending to an end portion side thereof, while forming a hole in said driver portion for inserting said pin therein, whereby positioning said driver portion and said surgical tool connection portion.

5. A manipulator, comprising:

a surgical tool portion;

a grip portion provided on said surgical tool portion; and a driver portion for driving said grip portion provided on said surgical tool portion, wherein a surgical tool connection portion is provided between said surgical tool portion and said driver portion, and said surgical tool portion can be separated from or connected to, said driver portion and said surgical tool connection portion;

a screw means for connecting said surgical tool connection portion and said driver portion, forming a hole in a central portion of said surgical tool connection portion, and also hole at a position corresponding to said hole in said driver portion, respectively.

6. A manipulator, comprising:

a surgical tool portion;

a grip portion provided on said surgical tool portion; and a driver portion for driving said grip portion provided on said surgical tool portion, wherein a surgical tool connection portion is provided between said surgical tool portion and said driver portion, and said surgical tool portion can be separated from or connected to, said driver portion and said surgical tool connection portion, and said surgical tool connection portion has a joint for rotating said grip portion, wherein said joint has: two rotating members, disposed in opposing relation to each other, and each of the rotating members has a semicircular shape and is integrally formed with a tip of one of a base portion of the manipulator and a cylindrical portion of the manipulator; a driving means for driving one of said rotating members to make a rotating movement to the other thereof; a means for keeping a distance between rotation centers of said two rotating members constant; and a member for maintaining the length and phase of guiding wires used by the driver portion for driving the grip portion constant.

7. A manipulator, comprising:

a joint having a first link and a second link therein;

a rotating contact means for bringing said first and second links to rotate while being in contact with each other;

a guiding means for guiding a wire at an equal distance from each rotation center of said links when they rotate while being in contact with each other;

said wire being guided by said guiding means, and said wire passing through said guiding means; and a member for maintaining the length and phase of guiding wires used by the driver portion for driving a grip portion of the manipulator constant;

wherein said rotating contact means has a semicircular shape and is integrally formed with a tip of one of a base portion of the manipulator and a cylindrical portion of the manipulator.

* * * * *